United States Patent
Arunabha et al.

(10) Patent No.: US 7,586,014 B2
(45) Date of Patent: Sep. 8, 2009

(54) PROCESS FOR THE LIQUID PHASE SELECTIVE HYDROXYLATION OF BENZENE

(75) Inventors: Datta Arunabha, Dehradun (IN); S. Sakthivel, Dehradun (IN); Satyarthi Jitendra Kumar, Dehradun (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 12/075,614

(22) Filed: Mar. 11, 2008

(65) Prior Publication Data
US 2008/0234524 A1 Sep. 25, 2008

(30) Foreign Application Priority Data
Mar. 23, 2007 (IN) ............ 654/DEL/2007

(51) Int. Cl.
*C07C 37/60* (2006.01)

(52) U.S. Cl. ...................... 568/800; 568/803
(58) Field of Classification Search ........... 568/800, 568/823
See application file for complete search history.

(56) References Cited
OTHER PUBLICATIONS

Pillai et al (Chem Comm (2002) 2142-2143).*
Lemke et al (Applied Catalysis A, General (2003) 243(1) 41-51).*

\* cited by examiner

*Primary Examiner*—Sikarl A Witherspoon
(74) *Attorney, Agent, or Firm*—Ladas & Parry LLP

(57) ABSTRACT

The present invention provides an improved process for the liquid phase selective hydroxylation of benzene. The process provides a direct single step selective liquid phase hydroxylation of benzene to phenol using environment friendly green oxidant, hydrogen peroxide, and vanadyl pyrophosphate as the catalyst under mild reaction conditions. The process provides benzene conversion of 30-70% and selectivity for phenol of up to 100%.

7 Claims, No Drawings

PROCESS FOR THE LIQUID PHASE SELECTIVE HYDROXYLATION OF BENZENE

FIELD OF THE INVENTION

The present invention relates to an improved process for the liquid phase selective hydroxylation of benzene. Particularly, the present invention relates to an improved process for the liquid phase selective hydroxylation of benzene using hydrogen peroxide as the oxidant in the presence of vanadyl pyrophosphate as catalyst. More particularly, the present invention relates to an improved process for the liquid phase selective hydroxylation of benzene to phenol by using hydrogen peroxide as the oxidant, vanadyl pyrophosphate as the catalyst and acetonitrile as the solvent under mild conditions.

BACKGROUND OF THE INVENTION

Phenol is a very important chemical for the chemical industry due to its widespread use in the fields of resin, plastics, pharmaceuticals, agrochemicals etc. It is mainly used for the production of a large number of intermediates such as bisphenol, caprolactam, aniline, alkylphenol, chlorophenol, salicylic acid etc., which are then further used to produce epoxy resin for paints, polycarbonate plastics for CDs and domestic appliances, nylon, polyamides, antioxidants, surfactants, detergents, anticeptics, medicines etc. At present phenol is mainly produced by the three steps Cumene Process. However, the process has several disadvantages such as poor ecology, formation of an explosive intermediate (cumene hydroperoxide), multi-step character which makes it difficult to achieve high phenol yield w.r.t. benzene. Moreover a major problem with this process is that it produces phenol and acetone in 1:1 molar ratio, but now demand for phenol is outpacing the demand for acetone and oversupply of acetone is driving its price down and also hurting the economics of phenol as well. This concern is the impetus for researchers to develop a direct single step co-product free and environment friendly route to phenol.

There are reports on the production of phenol by direct hydroxylation of benzene using vanadium containing catalyst and other catalyst but to the best of our knowledge there is no reference for the use of vanadyl pyrophosphate for this purpose.

Reference may be made to article in the Journal of Physical Chemistry, 1983, 87, 903-905, in which Japanese workers reported the use of nitrous oxide for the hydroxylation of benzene to phenol—using a vanadium pentoxide/silica catalyst at 550° C. to achieve 10% benzene conversion and 70% phenol selectivity.

Reference may also be made to world patents WO9527691, 1995 and WO9527560, 1995 wherein Kharitonov, A. S., Panov, G. I.; et al developed a one step process for the manufacture of phenol from benzene using nitrous oxide as the oxidant and ZSM-5 and ZSM-11 as the catalyst. The drawbacks of this process are deactivation of catalyst, loss of selectivity of catalyst and side reaction (combustion of benzene by nitrous oxide). It is economically attractive only if $N_2O$ is available as the by-product of some other process such as the two step oxidation of cyclohexane to adipic acid.

Reference may be made to article in J. Chem. Soc. Chem. Commun., 1992, 1446-1447 wherein Tatsumi et al. describe a process for the preparation of phenol from benzene with $H_2$ and $O_2$ which uses a catalyst consisting of palladium supported on TS-1. Operating according to this process, a conversion of benzene of 0.07% is obtained with a turnover of palladium of 13.5.

Another reference may be made to European patent EP0894783, 1998, wherein a process for the synthesis of phenol by catalytic oxidation of benzene in the presence of titanium silicalite and by $H_2O_2$ prepared in situ by reaction of oxygen carbon monoxide and water in the presence of catalytic complexes consisting of palladium with a nitrogenated ligand and a non-coordinating counter-ion. The selectivity of benzene to phenol is greater than 95%, but benzene conversions were only 1-2%.

Reference may be made to the article in Journal of Molecular Catalysis A: Chemical 253 (2006) 1-7, wherein phenol is prepared by the homogenous liquid-phase direct catalytic oxidation of benzene at room temperature in acetonitrile solvent using sodium metavanadate as the catalyst and hydrogen peroxide as the oxidant. Phenol yield of 13.5% with a selectivity of 94% was reported.

Reference may be made to Ind. Eng. Chem. Res. 1999, 38, 1893-1903, wherein phenol was synthesized by direct liquid phase benzene hydroxylation by $H_2O_2$ using V-MCM-41 as the catalyst under mild conditions. Operating according to this process, a conversion of benzene of 13% and selectivity for phenol of 48% was obtained.

Another reference may be made to article in Applied Clay Science 33 (2006) 1-6, wherein selective direct hydroxylation of benzene with hydrogen peroxide to phenol was carried out on a clay-supported vanadium oxide catalyst. Under mild reaction conditions at 313 K, high selectivity to phenol of 94% was obtained but conversion of benzene was only 14%.

The drawback of the processes reported so far is that they do not exhibit sufficiently high conversions of benzene for high selectivity of phenol to be of interest for industrial application. In addition, the catalysts used have a limited activity under the operating conditions. There is, therefore, an evident necessity for further improvements in the process for the selective conversion of benzene to phenol.

OBJECTIVES OF THE INVENTION

The main object of the present invention is to provide a process for the preparation of phenol by liquid phase selective hydroxylation of benzene using hydrogen peroxide as the oxidant and vanadyl pyrophosphate as the catalyst.

Another object of the present invention is to provide an improved process, which selectively gives phenol from benzene with high conversion.

Yet another object of the present invention is to provide a process which works under mild conditions for the synthesis of phenol.

Yet another object of the present invention is to provide a process which uses environment friendly green oxidizing agent, $H_2O_2$ for the synthesis of phenol.

SUMMARY OF THE INVENTION

Accordingly the present invention provides an improved process for the liquid phase hydroxylation of benzene which comprises reacting benzene with $H_2O_2$ in an organic solvent with molar ratio of benzene to $H_2O_2$ in the range of 1:2 to 1:5, in the presence of vanadyl pyrophosphate catalyst with benzene to catalyst molar ratio in range of 400-1600, at temperature of 50-70° C., while agitating the reaction mixture, for a period of 1-12 hours, followed by cooling in cold water at a temperature of 0 to 10° C. to obtain the desired products.

In another embodiment of the present invention, the molar ratio of benzene to $H_2O_2$ is preferably in range of 1:2 to 1:3.5.

In an embodiment of the present invention the molar ratio of benzene to catalyst is in range of 600-1200.

In another embodiment of the present invention the reaction temperature used is in the range of 50-60° C.

In yet another embodiment the reaction time used is preferably in the range of 7-12 hours.

In yet another embodiment the conversion of benzene to phenol is in the range of 30-70%.

In yet another embodiment the selectivity of the phenol obtained is 100%.

DETAIL DESCRIPTION OF THE INVENTION

The present invention provides a process for the production of phenol by liquid phase selective hydroxylation of benzene using hydrogen peroxide as the oxidant and vanadyl pyrophosphate as the catalyst which involves the following steps:
1. Synthesis of a VPO precursor $VOHPO_4.0.5H_2O$ from $V_2O_5$ keeping the PN ratio of 1.0-1.2,
2. Calcinations of the above precursor in nitrogen atmosphere at 400-600° C. for 4-6 hour to obtain a vanadyl pyrophosphate phase,
3. Benzene hydroxylation by agitating a mixture consisting of benzene ranging from 30-50 mmol and vanadyl pyrophosphate as catalyst along with $H_2O_2$ in 20 ml acetonitrile for 7 to 12 hour to obtain phenol, The reaction temperature is preferably in the temperature range of 50-70° C.

The molar ratio of the substrate to catalyst is preferably taken in the range of 600-1200.

The molar ratio of the substrate to $H_2O_2$ ratio is preferably used in the range of 1:2 to 1:5.

The benzene conversion is obtained 30 to 70 W % and selectivity to phenol approaching 100%.

The detailed steps of the process are:

About 0.05 mmol of catalyst was taken in 100 ml two neck R.B. flask containing 20 ml acetonitrile and 40 mmol of benzene to which 70 mmol of $H_2O_2$ was added. Then the reaction mixture was stirred while agitating at 60° C. for 1.5 hour and another 70 mmol of $H_2O_2$ was added. The reaction mixture was, then, agitated for another 7 hours. After completion of the reaction, the reaction mixture was cooled in cold water at a temperature of 0 to 10° C. and analysed by GC fitted with a capillary column and FID detector.

The following examples are given by way of illustration of the working of the invention in actual practice and should not be construed to limit the scope of the present invention in any way.

EXAMPLE-1

This example describes the hydroxylation of benzene by hydrogen peroxide using vanadyl pyrophosphate as the catalyst.

Process Conditions

Catalyst: 0.05 mmol

Benzene: 40 mmol

Acetonitrile: 20 mL $H_2O_2$: 140 mmol

Temperature: 60° C.

Product Analysis:

Benzene conversion: 53%

Yield of phenol: 53%

Selectivity for phenol: 100%

EXAMPLE-2

This example describes the effect of temperature on yield and selectivity of phenol. The product analysis presented in Table-1.

Process Conditions:

Catalyst: 0.05 mmol

Benzene: 40 mmol

Acetonitrile: 20 mL $H_2O_2$: 140 mmol

TABLE 1

Effect of temperature on benzene conversion, phenol yield and selectivity

| Temperature | Benzene | Phenol | |
|---|---|---|---|
| (° C.) | conversion (%) | Yield (%) | Selectivity (%) |
| 50 | 35 | 35 | 100 |
| 60 | 54 | 54 | 100 |
| 70 | 45 | 45 | 99 |

The above Table-1 shows the yield of phenol was highest at 60° C. with 100% selectivity and hence the optimum temperature for the present process was chosen, as 60° C.

EXAMPLE-3

This example demonstrates the effect of the amount of $H_2O_2$ on yield and selectivity of phenol. The product analysis is presented in Table-2.

Process Conditions:

Catalyst: 0.05 mmol

Benzene: 40 mmol

Acetonitrile: 20 mL

Temperature: 60° C.

TABLE 2

Effect of amount of $H_2O_2$ on benzene conversion phenol yield and selectivity

| Substrate/$H_2O_2$ | Benzene | Phenol | |
|---|---|---|---|
| ratio | conversion (%) | Yield (%) | Selectivity (%) |
| 1:2 | 12 | 12 | 100 |
| 1:3 | 43 | 43 | 100 |
| 1:3.5 | 53 | 53 | 100 |
| 1:4 | 67 | 60 | 90 |

The experimental results reported in Table-2 show the increase of yield of phenol with increase in amount of $H_2O_2$, but the selectivity was decreased. The optimum amount of $H_2O_2$ required for this process is 140 mmol.

EXAMPLE-4

This example illustrates the result of effect catalyst amount on the conversion of benzene. The product analysis presented in Table-3.

Process Conditions:

Benzene: 40 mmol

Acetonitrile: 20 mL $H_2O_2$: 140 mmol

Temperature: 60° C.

TABLE 3

Effect of catalyst amount on the conversion of benzene and yield and selectivity for phenol

| Substrate/Catalyst Ratio | Benzene conversion(%) | Phenol Yield (%) | Selectivity (%) |
|---|---|---|---|
| 400 | 45 | 45 | 99 |
| 800 | 53 | 53 | 100 |
| 1600 | 40 | 40 | 100 |

From the above table-3, it is shown that the conversion of benzene is highest when the substrate/catalyst ratio was 800.

EXAMPLE-5

This example demonstrates the recycleability of the catalyst. The phenol yield patterns of fresh and recycled catalysts are given in Table-5. After the completion of the reaction, the reaction mixture was extracted with ether. The aqueous layer was separated and dried in oven at 120° C. and the solid residue was as used. The results of using the recycled catalyst are shown in Table-4.

Process Conditions:

Catalyst: 0.05 mmol

Benzene: 40 mmol

Acetonitrile: 20 mL $H_2O_2$: 140 mmol

Temperature: 60° C.

TABLE 4

Effect of catalyst recycling on benzene conversion and yield and selectivity for phenol

| Catalyst | Benzene conversion (%) | Phenol Yield (%) | Selectivity (%) |
|---|---|---|---|
| Fresh | 53 | 53 | 100 |
| One time recycled | 43 | 43 | 100 |
| Two time recycled | 41 | 41 | 100 |

The recyclability of the catalyst is evident from the above results.

The main advantages of the present invention are:
1. The process of the present invention converts benzene to phenol in a single step with a single catalyst.
2. The process provides not only good conversion of benzene but also high selectivity for phenol.
3. The oxidizing agent, $H_2O_2$, used in the process is ecofriendly and gives only water as the side product.
4. The process is performed under very mild conditions of temperature and pressure.
5. The catalyst is used in very low amounts.

The invention claimed is:

1. A process for the liquid phase hydroxylation of benzene which comprises reacting benzene with $H_2O_2$ in an organic solvent with molar ratio of benzene to $H_2O_2$ in the range of 1:2 to 1:5, in the presence of vanadyl pyrophosphate catalyst with benzene to catalyst molar ratio in range of 400-1600, at temperature of 50-70° C., while agitating the reaction mixture, for a period of 1-12 hours, followed by cooling in cold water at a temperature of 0 to 10° C. to obtain the desired products.

2. A process according to claim 1, wherein the molar ratio of benzene to $H_2O_2$ is in range of 1:2 to 1:3.5.

3. A process according to claim 1, wherein the molar ratio of benzene to catalyst is in range of 600-1200.

4. A process according to claim 1, wherein the reaction temperature used is in the range of 50-60° C.

5. A process according to claim 1, wherein the reaction time used is preferably in the range of 7-12 hours.

6. A process according to claim 1, wherein the conversion of benzene to phenol is in the range of 30-70%.

7. A process according to claim 1, wherein the selectivity of the phenol obtained is 100%.

* * * * *